United States Patent [19]
Clement et al.

[11] Patent Number: 5,227,560
[45] Date of Patent: Jul. 13, 1993

[54] CHLORINATION AND ELIMINATION PROCESS AND SOME PRODUCTS THEREOF

[75] Inventors: Katherine S. Clement; W. Frank Richey, both of Lake Jackson; Marlin E. Walters, West Columbia, all of Tex.

[73] Assignee: The Dow Chemical Company, Midland, Mich.

[21] Appl. No.: 788,902

[22] Filed: Nov. 7, 1991

[51] Int. Cl.$^5$ .................................................. C07C 5/00
[52] U.S. Cl. ................................... 585/500; 585/469; 585/641; 570/226; 570/230
[58] Field of Search ................... 585/641, 469, 500; 570/226, 227, 228, 230

[56] References Cited

U.S. PATENT DOCUMENTS

| | | | |
|---|---|---|---|
| 3,225,106 | 12/1965 | Rabinowitz | 260/649 |
| 3,399,241 | 8/1968 | Smith | 260/633 |
| 3,484,482 | 12/1969 | Schmerling | 260/544 |
| 3,627,731 | 12/1971 | Curcio et al. | 260/651 R |
| 3,726,932 | 4/1973 | Mullin et al. | 260/654 R |
| 3,830,862 | 8/1974 | Meyers et al. | 260/668 C |
| 3,876,689 | 4/1975 | Meyers et al. | 260/503 |
| 3,896,164 | 7/1975 | Meyers et al. | 260/514 J |
| 3,935,289 | 1/1976 | de Radzitzky d'Ostrowick et al. | 260/660 |
| 3,949,001 | 4/1976 | Meyers et al. | 260/607 A |
| 3,953,494 | 4/1976 | Meyers et al. | 260/468 R |
| 3,992,432 | 11/1976 | Napier et al. | 260/465.1 |
| 4,008,287 | 2/1977 | Verbrugge et al. | 200/648 D |
| 4,105,702 | 8/1978 | Mullin et al. | 260/658 R |
| 4,132,611 | 1/1979 | Baizer et al. | 204/259 R |
| 4,192,822 | 3/1980 | Sweeney et al. | 260/653 |
| 4,226,783 | 10/1980 | Marsh | 260/351 |
| 4,297,514 | 10/1981 | Ma | 568/321 |
| 4,467,122 | 8/1984 | Szabolcs | 568/727 |
| 4,593,144 | 6/1986 | Chupp et al. | 568/936 |
| 4,675,458 | 6/1987 | Riemann et al. | 568/727 |
| 4,684,678 | 8/1987 | Schultz et al. | 523/461 |
| 4,922,038 | 5/1990 | Krespan et al. | 570/175 |
| 4,931,594 | 6/1990 | Knebel et al. | 568/727 |

OTHER PUBLICATIONS

Jonczyk et al: "Reactions of Carbon Tetrachloride with Carbon Acids Catalytic Two-Phase System", Journ. Org. Chem. 1979, vol. 44, pp. 1192-1194.

Lauritzen et al: "Chlorinations with Carbon Tetrachloride under Conditions of Phase Transfer Catalysis", Acta. Chem. Scand., 1981 vol. 35, pp. 263-268.

Reeves et al; "Halogenation by Phase Transfer Catalysis" Israel Jour. Chem., 1985, vol. 26, pp. 225-228.

CA 28:4392 (1934).

CA 72:66438s (1970).

CA 90:151235q (1979).

CA 105:225897j (1986).

Ida Smedley in *J. Chem. Soc.* 87 (1905) pp. 1249-1255.

Ray and Albertson in *J. Am. Chem. Soc.*, 70, pp. 1154-1155, 1954.

Greenhow, Harris, and White in *J. Chem. Soc.*, pp. 3116-3121 (1954) (CA50:263).

Ol'dekop and Kalinina in *Zhurnal Obshchei Khimii*, 30, pp. 3358-3361 (1960) (CA 55:18632).

Herbert O. House in *Modern Synthetic Reactions*, 3, pp. 156-162 (1965).

Makoszu, et al. in *Tetrahedron Lett.*, 53 (1969) pp. 4659-4662.

(List continued on next page.)

*Primary Examiner*—Asok Pal
*Assistant Examiner*—P. Achutamurthy

[57] ABSTRACT

Active methine compounds are chlorinated by contacting such compounds with a perchloroalkane and aqueous base in the presence of a phase transfer catalyst which is an tetraalkylonium hydroxide. Chlorinated products, preferably tertiary alkyl chloro compounds, are produced. The tertiary alkyl chloro compounds are useful in elimination reactions, preferably reactions with base, to form unsaturated compounds, particularly compounds having a vinylidene or exomethylene group.

28 Claims, No Drawings

OTHER PUBLICATIONS

P. W. Morgan in *Macromolecules* (1970) pp. 536-544.
Susuki and Tsuji in *J. Org. Chem.* 35, No. 9, (1970) pp. 2982-2986.
V. Heasley et al in *J. Org. Chem.* 39, No. 5, pp. 736-737 (1974).
A. Brandstrom in "Principles of Phase-Transfer Catalysis by Quaternary Ammonium Salts" in V. Gold et al(ed) *Advances in Physical Organic Chemistry* (1977) pp. 267-330.
E. Dehmlow et al in *Tetrahedron Lett.* 27 (1977) pp. 2361-2364.
Meyers et al in *Cayalysis in Organic Syntheses* pp. 197-278 (1977).
Alneri, Bottaccio, and Carletti in *Tetrahedron Lett.* 24, pp. 2117-2118 (1977).
Arnold and Kulenovic in *J. Org. Chem* 43, No. 19, (1978) pp. 3687-3689.
Magid et al in *J. Org. Chem.*, 44, No. 3, pp. 359-363 (1979).
Jonczyk, Kwast, and Makosza in *J. Org. Chem,* 44 No. 7 (1979) pp. 1192-1194.
Lauritzen et al in *Acta Chemical Scandinavica* 35, pp. 263-268 (1981).
Chen et al in *Journal of App. Polmer Source* vol. 27, 3289-3312 (1982).
Dehmlow and Dehmlow in *Phase Transfer Catalysis* pp. 1-22 (1983).
Reeves et al in *Israel Journal of Chemistry* 26, pp. 225-228 (1985).
Chupp et al, in *Synthesis* 1986 (2) pp. 224-226.

CHLORINATION AND ELIMINATION PROCESS AND SOME PRODUCTS THEREOF

This invention relates to chlorination and elimination, particularly to chlorination and elimination of chlorine from an organic compound having an active methine group.

It is often difficult to form compounds having unsaturation in a position desired for further reaction. For instance, chlorination processes often result in chlorine on ring atoms isolated from other ring substituents such that subsequent elimination is impossible (e.g. aromatic chlorines) or leads to endocyclic unsaturation rather than exocyclic unsaturation. Compounds having exocyclic substitution, however, are generally more useful, for instance, in preparing addition polymers and in alkylation reactions.

Chlorinations of compounds having an active methine structure such as 9-methylfluorene using common chlorination agents such as chlorine, sulfuryl chloride, N-chlorosuccinimide and phosphorus pentachloride are generally disadvantageous because the products of such reactions exhibit substitution on the aromatic rings, instead of substitution of the acidic proton. Therefore, it is not feasible to prepare 9-chloro-9-methylfluorene and analogous compounds such as 1-chloro-1-ethylindene using conventional chlorination technology.

The compound 9-methylenefluorene was reported by Ferrer (*Anales Soc. Espan. Fis. Quim.* 1922, 20, 459, *Chem Abstr.* 17, 3177 (1922) and *Ber.* 55, 3317 (1922)) as arising from distillation of 9-methyl-9-hydroxyfluorene in vacuo in the presence of aluminum phosphate. The compound was not isolated at that point, but was brominated to alpha,9-dibromomethylfluorene. The author states that the compound was debrominated by refluxing with zinc in alcohol to give 9-methylenefluorene as crystals (melting point 53° C.) which were stable for several hours. He also reported the production of a polymeric material. Sieglitz and Jassoy (*Ber.* 55, 2032 (1922)) prepared 9-methylenefluorene by distilling fluoryl-9-methylurethan with calcium oxide in vacuo or in an atmosphere of hydrogen. They reported a melting point of 46°–48° C. for the product and also reported the production of some polymeric material. The compound 9-ethylidenefluorene was reported by Daufresne (*Bull. Soc. Chim*, [4]1, 1233 (1907)) as arising from the dehydration of 9-hydroxy-9-ethylfluorene with hydrogen chloride. He reported that the compound was unstable and oxidized spontaneously in air to form an oxide which exploded at 100° C. Attempts to generate 9-methylenefluorene by the same method from 9-hydroxy-9-methylfluorene were unsuccessful. Courtot (*Ann. Chim.* [9]4, 218 (1915) and *Compt. Rend.* 152, 1493 (1911)) prepared derivatives of 9-methylenefluorene by the action of ketones and aldehydes on 9-fluorylmagnesium bromide and subsequent dehydration of the resulting carbinols by refluxing in methanol with hydrogen chloride. Thiele and Henle (*Ber.* 33 851 (1900) and Ann. 347, 290 (1910)) prepared mono-aromatic derivatives of 9-methylenefluorene by condensing aromatic aldehydes with fluorene using sodium methoxide or ethoxide.

Fluorenone can be reacted with Grignard reagents to prepare 9-alkylfluorenols (See, for example, Ferrer). These 9-alkylfluorenols were reported to be easily converted to the 9-halo-9-alkylfluorenes by treatment with halogen acids (Ferrer, *Chem. Abstr.* 17 3177 (1922); Wieland and Krause, Ann. 443, 129 (1925) and Ferrer, Wieland, and Reindel *Ber.* 55 3317 (1922)). When warmed to 80° C., the material gave off hydrochloric acid gas and polymerized. If instead, the material was dissolved in alcohol and boiled briefly, 9-methylenefluorene could be obtained. Alcohol can also react to replace the halogen.

A procedure for the preparation of 9,9-dichlorofluorene directly from fluorene, without fluorenone as an intermediate, was reported by Reeves et al. in Israel J. Chem. 26, 225, (1985). Tetrabutylammonium bromide was used as a phase transfer catalyst to chlorinate such compounds as fluorene, phenylpropanone, acetophenone, 1-chloroacetophenone, p-methoxyacetophenone, benzoin ethyl ether, desyl chloride, p-nitroacetophenone, deoxybenzoin, and xanthene using carbon tetrachloride in an organic phase as chlorine source with an aqueous hydroxide phase. It was reported that use of potassium carbonate in the aqueous phase in the attempted chlorination of p-nitroacetophenone resulted in no reaction. Using this reaction for the chlorination of fluorene, Reeves et al. reported a 51.9 percent yield of 9,9-dichlorofluorene. Other reaction conditions and time for the chlorination of fluorene are not given. A 57 percent yield was reported by Reeves for production of xanthone from xanthene using the procedure.

Tertiary chloro-compounds such as 9-chloro-9-methylfluorene are eliminated by such means as boiling in alcohol (Wieland and Krause, *Ann.*, 443, 129 (1925)). This, however, exposes the products to acid conditions which can promote uncontrolled polymerization.

It would be desirable to have a process for chlorinating and eliminating chlorine from compounds which have an active methine group such that replacement of the acidic hydrogens and subsequent elimination thereof is the predominant reaction. The reaction would be especially useful for forming exocyclic unsaturation. Advantageously, the process would not expose the reactants or products to reagents or conditions which promote polymerization or deterioration thereof.

SUMMARY OF THE INVENTION

The invention is a process for preparing an unsaturated compound comprising (a) contacting a compound having at least one active methine group with at least one perchloroalkane and aqueous base in the presence of a phase transfer catalyst which is an tetraalkylonium hydroxide such that a tertiary alkyl chloro product is produced and (b) contacting the tertiary alkyl chloro product with a base such that the tertiary chlorine atom is eliminated to form an unsaturated compound. A tertiary alkyl chloro product is produced in a process comprising contacting at least one compound having an active methine group with at least one perchloroalkane and aqueous base in the presence of a phase transfer catalyst which is an tetraalkylonium hydroxide. The invention includes a process for eliminating at least one chlorine on the tertiary alkyl chloro compound by contacting said tertiary alkyl chloro compound with a base. The base used for elimination is preferably the same one used for the chlorination such that both reactions occur in one process.

The process of the invention is particularly useful for preparation of compounds such as 9-methylenefluorene which are unstable to acid.

This method advantageously involves the formation of the alkene functionality under conditions of basic pH to prevent cationic polymerization, such as through dehydrohalogenation of an alkyl chloride with base.

DETAILED DESCRIPTION OF THE INVENTION

The process of the invention is useful for chlorinating compounds which have an active methine group which is a carbon atom having one acidic proton. It has been stated by Reutov et. al. (O. A. Reutov, I. P. Beletskaya and K. P. Butin, CH-ACIDS, Pergamon Press, New York, N.Y., 1978.) that "almost any organic compound can ionize in solution to give carbanions, that is, negatively charged species whose charge is totally or more often partially localized on one of the carbon atoms". When certain substituents are part of the hydrocarbon structure and are bonded to a saturated carbon atom which also bears a hydrogen atom this hydrogen atom is relatively acidic. Examples of such substituents are unsaturated functional groups such as vinyl, nitro, carbonyl, cyano, sulfone, or phenyl groups. The inductive electron withdrawing ability and the ability of these substituents to delocalize the negative charge remaining when a proton has been removed are responsible for the acidity of the carbon-hydrogen bond. These compounds are often referred to as active methine compounds. Such active methine compounds are preferred for use in the practice of the invention: more preferred are compounds having an active methine group (—CH—, a carbon having one hydrogen and three other substituents) adjacent at least one nitro, carbonyl, cyano, sulfone, or phenyl group, most preferably adjacent at least two such groups. Exemplary of such compounds are 9-alkylfluorenes such as 9-methylfluorene, 9-ethylfluorene, ring-substituted 9-alkylfluorenes, 1-alkyl indenes such as 1-methylindene, 9-alkylxanthenes such as 9-methylxanthene, 10-alkylanthrones, 1-alkyl-2,4-cyclopentadienes, such as 1H,1-methylcyclopentadiene, α-alkyl deoxybenzoins, α-alkyl phenylacetonitriles, 9-alkyldihydroanthracenes, [9H,10H]9,10-dialkyl dihydroanthracenes, 1-alkyl-1-phenyl-2-propanones, α,α-benzyl ketone, 1,4-dialkylphenylene, and the like. The process of the invention is particularly useful for compounds for which the replacement of the acidic proton with chlorine is not easy under conventional chlorination conditions including 9-alkylfluorene, 1-alkylindene, 9-alkylxanthene, 10-alkylanthrone and the like, preferably 9-alkylfluorene and its derivatives which are ring-substituted, most preferably 9-alkylfluorene. For elimination to make unsaturated compounds, the methine group preferably has at least one alkyl or alkaryl group bonded to the methine carbon; such groups preferably have from one to about 12 carbon atoms, more preferably from one to about 6, most preferably from one to about 3 carbon atoms, particularly one carbon atom, advantageously a methyl group. For elimination to take place, the group preferably has at least one hydrogen atom on a, preferably saturated, carbon bonded to the methine group, that is a hydrogen atom vicinal to the chlorine. Such target compounds are unsubstituted or inertly substituted, that is having substituents which do not undesirably interfere with the chlorination or subsequent reactions. Such substituents include alkyl, halo, nitro, cyano, carboxyl, thio, sulfoxide, sulfone, carbonyl, ether, and aryl groups, as well as other substituents not having a hydroxyl, primary or secondary amino, or mercapto group.

The target compound is chlorinated by contacting it with a perchloroalkane such as carbon tetrachloride, hexachloroethane, or benzotrichloride and the like as the chlorine source. Carbon tetrachloride is the preferred chlorine source and is used herein to exemplify perchloroalkanes, but not to limit the process thereto. The perchloroalkane is suitably used in any amount which provides sufficient chlorine for the reaction, and may also be present in an amount sufficient to dissolve the compound being chlorinated (target compound). It is, however, unnecessary that there be sufficient perchloroalkane to dissolve the target compound. When the compound to be chlorinated has a low solubility in the perchloroalkane, it is preferable to use a solvent miscible in the perchloroalkane which dissolves significant amounts of the target compound. Preferably the perchloroalkane is used in an amount from about 1:1 to about 100:1 based on the molar concentration of reactant (target compound), more preferably from about 2:1 to about 50:1, most preferably from about 2:1 to about 10:1 based on the molar concentration of the target compound.

When an additional solvent is used, it is preferably one which is miscible with the perchloroalkane and which dissolves the target compound and, conveniently, is not undesirably affected by the reaction conditions. Such solvents include methylene chloride, ethylbenzene, cumene, chlorobenzene, tetrahydrofuran and the like. Such a solvent is conveniently used in an amount sufficient to obtain the maximum concentration of the target compound but not so little that the product would precipitate from the reaction mixture.

The target compound is contacted with the perchloroalkane in the presence of a base strong enough to deprotonate the target compound, that is, capable of forming the conjugate base of the target compound. Such bases include inorganic and organic hydroxides and any other strong bases compatible with water, preferably alkali metal hydroxides or tetraalkylammonium hydroxides more preferably alkali metal hydroxides, most preferably sodium hydroxide. Alkali metal hydroxides are preferred because they have good solubility in water and relatively low equivalent weight. Sodium hydroxide is more preferred because of commercial availability. The base is advantageously in aqueous solution because of ease of removal from product. The solution is suitably of a concentration sufficient to promote the reaction at a desirable rate, preferably from about 10 percent to about 80 percent, more preferably from about 20 percent to about 50 percent, most preferably from about 30 percent to about 40 weight percent base in water. Sodium hydroxide solutions of 40 percent and above often result in emulsions which are difficult to handle. The aqueous solution of base and perchloroalkane are suitably present in any ratio sufficient to promote the reaction at a desirable rate. A desirable rate is generally one sufficient to complete the reaction in the desired time but insufficient to cause excessive or uncontrollable exothermic heating of the reaction mixture.

Contrary to the teachings of Reeves et al., Israel J. Chem. 26, 225, (1985) wherein a large excess of base was used with a tetrabutylammonium bromide phase transfer catalyst, in the process of the invention it is surprisingly observed that much less than an equivalent of base is needed. The preferable amount of base as a function of the concentration of the target compound is 0.001 to 1000, more preferably from about 0.01 to about 100, most preferably from about 0.1 to about 10 molar ratio. Less than a stoichiometric amount of base is preferred because it leaves more room in the reactor to make product and there is less base to dispose of after the reaction.

Because the target compound is not sufficiently soluble in the aqueous base, a phase transfer catalyst is used. Surprisingly good yields and low reaction times are noted when the phase transfer catalyst is a tetraalkylammonium hydroxide such as tetrabutylammonium hydroxide, tetramethylammonium hydroxide, tetraethylammonium hydroxide, tetrapropylammonium hydroxide, benzyltrimethylammonium hydroxide, tributylmethylammonium hydroxide and the like, preferably the phase transfer catalyst is a tetraalkylammonium hydroxide wherein all alkyl groups have from about 1 to about 20 carbon atoms and are non-aromatic, more preferably the tetraalkylammonium hydroxide is tetrabutylammonium hydroxide or tributylmethylammonium hydroxide, most preferably tetra-n-butylammonium hydroxide because this catalyst brings the reaction to completion in the shortest time with the least amount of catalyst relative to the target compound.

The phase transfer catalyst is suitably present in any amount sufficient to give a desired rate of reaction, advantageously at least about 0.0001 mole ratio, preferably from about 0.0001 to about 1, more preferably from about 0.001 to about 0.1, most preferably from about 0.001 to about 0.05 molar ratio based on the number of moles of the target compound because this amount gives an acceptable rate of reaction and using more generally costs more and makes purification of the product more difficult. While the hydroxide phase transfer catalyst is optionally admixed with other phase transfer catalysts, e.g. the halide salts, the phase transfer catalyst is preferably present in the hydroxide salt form in at least the concentrations noted.

Conveniently, the compound to be chlorinated is dissolved in the perchloroalkane, to which are added the aqueous base and phase transfer catalyst either sequentially in either order, simultaneously but separately or in admixture to form a reaction mixture. This order is convenient because it is observed that the solution of the compound in perchloroalkane is conveniently purged, e.g. with an inert gas such as nitrogen, helium, argon, neon, or hydrogen to remove oxygen to avoid production of an oxidized target compound as a by-product. Alternatively, the reagents are suitably mixed in any order such that all reactants are present at one time. The reaction mixture is preferably agitated by any means effective to maximize the surface area of the immiscible phases so that the reactants in each phase are repeatedly brought together.

When oxygenated (e.g. peroxide) products are not desired it is often preferable to exclude oxygen from the reaction. Oxygen is suitably excluded by any means within the skill in the art such as by maintaining a nitrogen blanket over the reaction mixture, such as by nitrogen sparging. Other inert gasses or the vapors of highly volatile organic compounds may be employed.

Any reaction conditions under which the chlorination takes place are suitable, but preferred temperatures are from about 0° C. to about 100° C., more preferably from about 15° C. to about 80° C., most preferably from about 25° C. to about 40° C. because at these temperatures the reaction proceeds rapidly and there is little degradation of the catalyst. Any effective pressure is suitable, at or near atmospheric pressure is generally convenient. High pressure is not harmful. Lower pressures are limited by the vapor pressures (boiling points) of the solvents employed.

Good mixing is important for rapid reaction. For instance at a mole ratio of sodium hydroxide to fluorene of 10:1; mole ratio of tetrabutylammonium hydroxide to fluorene of 0.02:1.0; mole ratio of carbon tetrachloride to fluorene of 2:1 and 25 weight percent fluorene in methylene chloride at 30° C. for the indicated times, the following table indicates the importance of stirring on yield of 9,9-dichlorofluorene (9,9-DCF).

| TIME (minutes) | at 500 RPM percent 9,9-DCF corresponding to 0.8 W/L | at 1500 RPM percent 9,9-DCF corresponding to 19.7 W/L | at 3000 RPM percent 9,9-DCF corresponding to 106 W/L |
| --- | --- | --- | --- |
| 0 | 0 | 0 | 0 |
| 1 | 73.1093 | 84.8193 | 95.7622 |
| 2 | 80.2118 | 89.1515 | 96.7862 |
| 3 | 84.6704 | 91.7289 | 97.1994 |
| 4 | 89.3134 | 93.3434 | 98.1167 |
| 5 | 91.7465 | 95.5317 | 98.1575 |
| 10 | 94.8384 | 95.7186 | 98.9512 |
| 15 | 96.2824 | 97.4078 | 99.053 |
| 20 | 96.9075 | 97.4977 | 99.0207 |
| 30 | 97.177 | 97.4588 | 99.086 |
| 60 | 98.1961 | 98.47 | 99.3304 |
| 120 | 96.3133 | 97.3576 | 99.0197 |

Thus, for relatively shorter reaction times, relatively faster mixing is preferred. While mixing is difficult to quantify, in a situation with relatively constant viscosities, power per unit volume (watts per liter) is indicative of the amount of mixing. These values were obtained using a Lightnin ™ LabMaster II ™ Model TSM2010 Mixer commercially available from Mixing Equipment Company, Avon Division, a unit of General Signal which directly measures the watts input into the mixer. Thus, in the practice of the invention, mixing preferably involves use of at least about 0.8 W/L, more preferably at least about 15.0 W/L, most preferably at least about 100 W/L. Such mixing is suitably accomplished by any means within the skill in the art such as by rotary, static (e.g. recirculating, e.g. by pump) or other mixing.

The reaction is preferably carried out using non-metallic vessels and equipment, that is not having exposed metals, because metals such as iron (including steel, even stainless steels such as those designated as 304 on 316 stainless steel), nickel and titanium are observed to inhibit the reaction. The term non-metallic vessels and equipment is used to include vessels and equipment lined with non-metallic materials such as polymers (including plastics, resins and glass). Thus the reaction preferably occurs in the substantial absence of such metals, that is in the absence of sufficient metal to undesirably inhibit the reaction, more preferably in the absence of other than incidentally present (not deliberately added) metals particularly iron, including 304 stainless steel and 316 stainless steel. These metals are believed to inhibit the tetraalkylammonium hydroxides; thus use of additional tetraalkylammonium hydroxide to replace that which is inhibited permits reaction in the presence of metals.

When the chlorination product is desired and it does not immediately undergo elimination under reaction conditions for the chlorination reaction, the product can be isolated by means within the skill in the art, preferably by washing the solution with water to remove catalyst, then evaporating the solvent. Products are usually solids and are optionally purified by crystallization.

The chlorination reaction is allowed to go to a predetermined degree of completeness, advantageously to completion as determined by cessation of an increase in concentration of product. At temperatures such as about 30° C., completion is observed after about 1 minute to 3 hours depending on catalyst concentration, caustic concentration, and degree of mixing or agitation.

Exemplary products include 9-chloro-9-methylfluorene, 1-chloro-1-methylindene, 1H,1-chloro-1-methylcyclopentadiene, 1-chloro-1-methylphenalene, 9H,10H,9,10-dichloro-9,10-dimethyldihydroanthracene, 9-chloro-9-methylxanthene and the like.

The product can be isolated by means within the skill in the art, preferably by washing the solution with water to remove catalyst, then evaporating the solvent. Products are usually solids and are optionally purified by crystallization. Isolation is, however, unnecessary for further reaction, especially elimination.

When the chlorination product is to undergo elimination, it is generally advantageous to allow that elimination to take place under essentially the conditions of the chlorination reaction. By essentially the same conditions is meant conditions (e.g. temperature, pressure, reactant concentrations) sufficiently similar to produce product in a yield within about 25 mole percent of the alternative conditions. However, additional base, stronger base or additional heat can be useful in achieving elimination when it is undesirably slow under chlorination conditions. The unsaturated product is preferably produced in the reaction mixture used for chlorination, but is alternatively isolated for further reaction. The elimination reaction is suitably conducted under any conditions effective for the elimination. Temperature and pressure are not critical. For instance, atmospheric pressure is advantageously convenient, but higher or lower pressures than atmospheric are suitable. Temperatures sufficient to achieve reaction are suitable, as are temperatures up to those sufficient to cause undesirable deterioration of the product or reactants. Preferred temperatures range from about 0° to about 100° C.

The base is suitable any base in any concentration sufficient to result in elimination of the chlorine atom to form a double bond, but preferably insufficient to result in undesirable deterioration of the product or reactants. Preferred bases are those used in the chlorination reaction, but pyridine, trimethylamine, triethylamine, potassium or sodium t-butoxide, potassium or sodium alkoxides, and the like are also suitable. Preferred concentrations (ratios) are from about 100:1 to about 1:2, more preferably from about 10:1 to about 1:1, most preferably from about 5:1 to about 1:1 based on equivalents of chloro compound or target compound.

Products are preferably compounds having a vinylidene group ($=CR_2$ wherein each R is independently H or an unsubstituted or inertly substituted alkyl, aryl, or alkaryl preferably of from 1 to about 12 carbon atoms, including exocyclic methylene (exomethylene) and vinyl groups). Exemplary products include 1-methyleneindene, fulvene, 9,10-dimethyleneanthracene, 9-methylenexanthene, 9-methylenefluorene, 1,2-diphenylbut-2-en-1-one, and 1-cyano-1,2-diphenylethene, preferably 9-methylenefluorene.

The elimination product is suitably isolated by means within the skill in the art such as by extraction, distillation, evaporation, crystallization and the like. The products are generally quite reactive and are advantageously protected from air and light. Undesired polymerization is advantageously prevented by the addition of inhibitors such as those useful in the handling of similar compounds such as styrene.

The catalyst (tetraalkylonium hydroxide) and/or the base (inorganic or organic hydroxides) are, optionally, conveniently recycled to prepare chloro compounds through many reaction cycles with no loss in efficacy. The catalyst is easily recovered from the reaction mixture after completion of the reaction by means known to those skilled in the art, such as extraction with water or other immiscible solvent having good solubility for the tetraalkylonium hydroxide, or alternatively by contacting the reaction solution with an acidic ion exchange resin to retain the catalyst as a salt followed by regeneration of the tetraalkylonium hydroxide by contacting the ion exchange resin with an aqueous hydroxide solution. In either case, the catalyst is conveniently isolated by evaporative removal of the solvent or is simply used without isolation if the concentration and the solvent are appropriate for the desired reaction. Reuse of the base is, for instance, accomplished by phase separation of the organic and aqueous phases after completion of the reaction and admixing or contacting fresh organic reaction mixture with the separated aqueous phase. Catalyst, either fresh or recovered, is then supplied and the reaction repeated. Recycle of catalyst and/or base is a major advantage since it reduces the amount of raw materials needed with corresponding reduction of waste to dispose.

Variations on conditions for the reaction, particularly the chlorination reaction, are as explained in copending U.S. application Ser. No. 07/789,232, which is incorporated herein by reference in its entirety.

What is claimed is:

1. A process for preparing an unsaturated compound comprising (a) contacting a compound having atleast one active methine group, hereinafter called the target compound, with atleast one perchloroalkane and aqueous base in the presence of a phase transfer catalyst which is a tetraalkyloniumhydroxide such that a tertiary alkyl chloro product is produced and (b) contacting the tertiary alkyl chloro product with a base such that the tertiary chlorine atom is eliminated to form a double bond between the methine carbon and an adjacent carbon atom.

2. The process of claim 1 wherein the tetraalkylonium hydroxide is tetrabutylammonium hydroxide, tetramethylammonium hydroxide, tetraethylammonium hydroxide, tetrapropylammonium hydroxide, benzyltrimethylammonium hydroxide, tributylmethylammonium hydroxide or a mixture thereof.

3. The process of claim 1 wherein the tetraalkylonium hydroxide is present in a ratio of from about 0.0001 to about 1 based on the number of moles of the target compound.

4. The process of claim 1 wherein the active methine compound has a methine group adjacent to at least one vinyl, nitro, carbonyl, cyano, sulfone, or phenyl group.

5. The process of claim 4 wherein the active methine compound has a methine group adjacent to at least two functional groups independently selected from vinyl, nitro, carbonyl, cyano, sulfone, and phenyl groups.

6. The process of claim 5 wherein the target compound is an unsubstituted or inertly substituted 9-alkylfluorene, 1-alkylindene, 9-alkylxanthene, 10-alkylanthrone, 1-alkyl-2,4-cyclopentadiene, α-alkyl deoxybenzoin, α-alkylphenylacetonitrile, 9-alkyldihydroanthracene. [9H,10H]9,10-dialkyl-dihydroanthracene, 1-alkyl-1-phenyl-2-propanone, α,α,benzyl ketone, 1,4-dialkylphenylene or mixture thereof.

7. The process of claim 6 wherein the target compound is an unsubstituted or inertly substituted 9-alkyl fluorene wherein the alkyl group has from 1 to about 6 carbon atoms.

8. The process of claim 6 wherein the target compound is an unsubstituted or inertly substituted 9-methylfluorene, 1-methylindene, 9-methylxanthene, 10-methylanthrone, 1-methyl-2,4-cyclopentadiene, α-methyl deoxybenzoin, α-methylphenylacetonitrile, 9-methyldihydroanthracene, [9H,10H]9,10-dimethyl-dihydroanthracene, 1-methyl-1-phenyl-2-propanone, α,α,benzylketone, 1,4-dimethylphenylene or mixture thereof.

9. The process of claim 8 wherein the target compound is 9-methylfluorene.

10. The process of claim 1 wherein the perchloroalkane is carbon tetrachloride, hexachloroethane, benzotrichloride or a mixture thereof.

11. The process of claim 10 wherein the perchloroalkane is carbon tetrachloride.

12. The process of claim 10 wherein the perchloroalkane is used in an amount of from about 1:1 to about 100:1 based on the molar concentration of target compound.

13. The process of claim 1 wherein an additional solvent for the target compound is used.

14. The process of claim 1 wherein there is mixing at a level of 0.8 Watts/Liter.

15. The process of claim 1 which takes place in a vessel with is non-metallic or lined with a non-metallic material and using equipment which is non-metallic or coated with a non-metallic coating.

16. The process of claim 1 which takes place in the substantial absence of exposed metals selected from iron, steel, copper, nickel, titanium, or mixtures thereof.

17. The process of claim 1 wherein the base is an organic or inorganic hydroxide.

18. The process of claim 17 wherein the base is an alkali metal hydroxide.

19. The process of claim 1 wherein steps (a) and (b) take place under the essentially the same reaction conditions of temperature, pressure and base concentration.

20. The process of claim 19 wherein steps (a) and (b) take place simultaneously.

21. The process of claim 1 wherein a product is not isolated between steps (a) and (b).

22. The process of claim 1 wherein in step (b) additional base is used.

23. The process of claim 22 wherein the base is an inorganic hydroxide.

24. The process of claim 22 wherein the base is a pyridine, trimethylamine, triethylamine, potassium or sodium t-butoxide, potassium or sodium alkoxide, or mixture thereof.

25. The process of claim 1 wherein in step (b) the base is present in a ratio of from about 100:1 to about 2:1 based on equivalents of tertiaryalkyl chloro compound or target compound.

26. The process of claim 1 wherein the product has a exomethylene group ($=CH_2$).

27. The process of claim 1 wherein the product is 1-methyleneindene, fulvene, 9,10-dimethyleneanthracene, 9-methylenexanthene, 9-methylene fluorene, 1,2-diphenylbut-1-en-1-one, and 1-cyano-1,2-diphenylethenes.

28. The process of claim 27 wherein the product is 9-methylene fluorene.

* * * * *